(12) United States Patent
Matsuo et al.

(10) Patent No.: US 11,814,652 B2
(45) Date of Patent: Nov. 14, 2023

(54) PLURIPOTENT STEM CELL DIFFERENTIATION-PROMOTING AGENT

(71) Applicant: Oriental Yeast Co., Ltd., Tokyo (JP)

(72) Inventors: Hidenori Matsuo, Nagahama (JP); Ayumi Ga, Nagahama (JP); Munehiro Yamada, Nagahama (JP); Yoshiya Tomimori, Nagahama (JP)

(73) Assignee: ORIENTAL YEAST CO., LTD., Tokyo (JP)

(*) Notice: Subject to any disclaimer, the term of this patent is extended or adjusted under 35 U.S.C. 154(b) by 515 days.

(21) Appl. No.: 16/981,628

(22) PCT Filed: Mar. 20, 2019

(86) PCT No.: PCT/JP2019/011827
§ 371 (c)(1),
(2) Date: Sep. 16, 2020

(87) PCT Pub. No.: WO2019/182044
PCT Pub. Date: Sep. 26, 2019

(65) Prior Publication Data
US 2021/0024897 A1    Jan. 28, 2021

(30) Foreign Application Priority Data
Mar. 22, 2018  (JP) ................... 2018-055186

(51) Int. Cl.
*C12N 5/074* (2010.01)
(52) U.S. Cl.
CPC ........ *C12N 5/0696* (2013.01); *C12N 2500/38* (2013.01)
(58) Field of Classification Search
CPC ............. C12N 5/0696; C12N 2500/38; C12N 5/0667; C12N 2501/999; C12N 5/0068; C12N 2500/40; A61K 31/706
See application file for complete search history.

(56) References Cited

U.S. PATENT DOCUMENTS 7,737,158 B2   6/2010  Imai et al.
10,548,913 B2*  2/2020  Normington ......... C07F 9/6561
(Continued)

FOREIGN PATENT DOCUMENTS

CN   104367587    2/2015
JP   2010-524457  7/2010
(Continued)

OTHER PUBLICATIONS

Shade C. The Science Behind NMN—A Stable, Reliable NAD+ Activator and Anti-Aging Molecule. Integr Med (Encinitas). Feb. 2020;19(1):12-14 (Year: 2020).*
(Continued)

*Primary Examiner* — Jeremy C Flinders
*Assistant Examiner* — Thomas R. Amick
(74) *Attorney, Agent, or Firm* — Hamre, Schumann, Mueller & Larson, P.C.

(57) ABSTRACT

The object of the present invention is to provide a material for efficiently obtaining differentiated cells from pluripotent stem cells. That is, the present invention relates to a pluripotent stem cell differentiation-promoting agent containing, as an active ingredient, a β-nicotinamide mononucleotide or a pharmacologically acceptable salt thereof, and a solvate thereof, and a method for differentiating pluripotent stem cells, including culturing pluripotent stern cells in a culture medium containing a β-nicotinamide mononucleotide or a pharmacologically acceptable salt thereof, and a solvate thereof.

16 Claims, 15 Drawing Sheets
Specification includes a Sequence Listing.

(56) References Cited

U.S. PATENT DOCUMENTS

2013/0011921 A1 1/2013 Hishida et al.
2015/0072416 A1* 3/2015 Cho .................. C12N 5/0696
435/377

FOREIGN PATENT DOCUMENTS

| | | |
|---|---|---|
| JP | 2015-507921 | 3/2015 |
| WO | 2008/129554 | 10/2008 |
| WO | 2011/102333 | 8/2011 |
| WO | 2012/056997 | 5/2012 |
| WO | 2013/121426 | 8/2013 |
| WO | 2014/146044 | 9/2014 |
| WO | 2018/143258 | 8/2018 |

OTHER PUBLICATIONS

Christina McKee, G. Rasul Chaudhry, Advances and challenges in stem cell culture, Colloids and Surfaces B: Biointerfaces, vol. 159, 2017, pp. 62-77 (Year: 2017).*

Gilbert SF. Developmental Biology. 6th edition. Sunderland (MA): Sinauer Associates; 2000. Early Mammalian Development. Available from: https://www.ncbi.nlm.nih.gov/books/NBK10052/ (Year: 2000).*

Idelson et al. Cell Stem Cell. 2009;5:396-408 (Year: 2009).*

Saito M, et al. Cytotechnology. Jan. 2013;65(1):105-18 (Year: 2013).*

Son, et al., "Nicotinamide Overcomes Pluripotency Deficits and Reprogramming Barriers", Stem Cells, 2013, vol. 31, p. 1121-1135.

Zhao, Yan et al., "Regenerative Neurogenesis After Ischemic Stroke Promoted by Nicotinamide Phosphoribosyltransferase-Nicotinamide Adenine Dinucleotide Cascade", Stroke, Jun. 9, 2015, vol. 46, No. 7, pp. 1966-1974.

Matsuo, Hidenori et al., "Effect of β-Nicotinamide mononucleotide in human pluripotent stem cells", Lecture Abstracts of the Annual Meeting of the Japanese Biochemical Society 2017, vol. 90th, IP-0891 (A concise explanation of relevance provided in the attached International Search Report).

Meng, Ya et al., "Nicotinamide Promotes Cell Survival and Differentiation as Kinase Inhibitor in Human Pluripotent Stem Cells", Stem Cell Reports, Dec. 11, 2018, vol. 11, pp. 1347-1356.

International Search Report of PCT/JP2019/011827, dated Jun. 25, 2019, 4 pages including English translation.

The extended European Search Report issued for European Patent Application No. 19771934.7, dated Oct. 21, 2021, 8 pages.

Office Action issued for Chinese Patent Application No. 201980029188.3, dated Jul. 8, 2023, 15 pages including English translation.

* cited by examiner

| β-NMN | 0mM | 0.1mM | 0.25mM |
|---|---|---|---|
| |  |  |  |

| β-NMN | 0mM | 0.1mM | 0.25mM |

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer of
      PPARgamma

<400> SEQUENCE: 1
gagcccaagt ttgagtttgc                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer of
      PPARgamma

<400> SEQUENCE: 2
tcaatgggct tcacattcag                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer of
      Adiponectin

<400> SEQUENCE: 3
cctggtgaga agggtgagaa                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer of
      Adiponectin

<400> SEQUENCE: 4
ctcctttcct gccttggatt                                                   20

<210> SEQ ID NO 5
<211> LENGTH: 26
<212> TYPE: DNA

```
<213> ORGANISM: Artificial Sequence
<220> FEATURE:
<223> OTHER INFORMATION: Description of Artificial Sequence: Primer of
      GAPDH

<400> SEQUENCE: 5
aacgggaagc ttgtcatcaa tggaaa                                          26

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer of
      GAPDH

<400> SEQUENCE: 6
gcatcagcag aggggggcaga g                                              21
```

|---|---|---|---|
| |  |  |  |

PLURIPOTENT STEM CELL DIFFERENTIATION-PROMOTING AGENT

TECHNICAL FIELD

The present invention relates to a material that promotes the differentiation of pluripotent stem cells and a method for differentiating pluripotent stem cells using the material.

Priority is claimed on Japanese Patent Application No. 2018-055186, filed Mar. 22, 2018, the content of which is incorporated herein by reference.

BACKGROUND ART

Pluripotent stem cells are undifferentiated cells that are capable of self-renewal and are capable of differentiating into various cells. In recent years, regenerative medicine in which pluripotent stem cells or cells differentiated from pluripotent stem cells are transplanted into damaged tissue of a patient to regenerate its function has been actively studied. Since regenerative medicine requires a large quantity of pluripotent stem cells and their differentiated cells, methods for efficiently proliferating pluripotent stem cells and methods for efficiently differentiating pluripotent stem cells has been actively developed.

As a method for promoting the differentiation of pluripotent stem cells, for example, it has been reported that differentiation of human stem cells into retinal pigment epithelial cells can be promoted by pre-culturing the human stem cells with nicotinamide (NAM) prior to culturing them in a differentiation-inducing culture medium containing the TGFβ superfamily (differentiation-inducing factor) (see, e.g., Patent Document 1). Further, it has also been reported that mesenchymal stem cells can be efficiently grown by, for example, culturing in a medium containing nicotinamide (NAM) and fibroblast growth factor 4 (FGF4) (see, e.g., Patent Document 2). It has also been reported that when artificial pluripotent stem cells (iPS cells) are cultured in the presence of NAM, since NAM inhibits the functions of sirtuin or PARP, iPS cells with a gene expression pattern similar to that of embryonic stem cells (ES cells) can be efficiently produced (see, e.g., Patent Document 3). Differentiated cells can be efficiently obtained by culturing pluripotent stem cells efficiently produced by these methods in a differentiation-inducing culture medium. In addition, it has been reported that NAM eliminates pluripotent loss of pluripotent stem cells and eliminates reprogramming obstacles (see, e.g., non-patent document 1).

On the other hand, nicotinamide mononucleotide (NMN) is a biosynthetic intermediate metabolite of the coenzyme $NAD^+$. Recently, it has been reported that NMN has the effect of improving insulin secretory capacity in aged mice, and the effect of dramatically improving insulin sensitivity and secretion in mouse models of type 2 diabetes caused by a high-fat diet and aging (see, e.g., Patent Document 4), and markedly enhancing mitochondrial function in aged muscles. Furthermore, it has been reported that administration of NMN is useful in improving and preventing obesity, increasing blood lipid levels, decreasing insulin sensitivity, decreasing memory capacity and symptoms of various age-related diseases causing eye function-deterioration such as macular degeneration (see, e.g., Patent Document 5).

PRIOR ART LITERATURE

Patent Documents

[Patent Document 1] Published Japanese Translation No. 2010-524457 of the PCT International Publication

[Patent Document 2] Published Japanese Translation No. 2015-507921 of the PCT International Publication

[Patent Document 3] PCT International Publication No. WO2011/102333

[Patent Document 4] U.S. Pat. No. 7,737,158

[Patent Document 5] PCT International Publication No. WO2014/146044

Non-Patent Document

[Non-patent Document 1] Son, et al., STEM CELLS, 2013, vol. 31, p. 1121-1135.

DISCLOSURE OF INVENTION

Problems to be Solved by the Invention

The present invention is intended to provide a material for efficiently obtaining differentiated cells from pluripotent stem cells and a method for promoting the differentiation of pluripotent stem cells using the material.

Means for Solving the Problems

As a result of intensive studies to solve the above problems, the present inventors have discovered that more differentiated cells can be obtained by differentiating pluripotent stem cells in the presence of a β-nicotinamide mononucleotide (β-NMN) and completed the present invention.

That is, the present invention provides the following pluripotent stem cell differentiation-promoting agent, a method for differentiating pluripotent stem cells, and a method for promoting differentiation of pluripotent stem cells.

[1] A pluripotent stem cell differentiation-promoting agent, comprising, as an active ingredient, a β-nicotinamide mononucleotide or a pharmacologically acceptable salt thereof, and a solvate thereof.

[2] The pluripotent stem cell differentiation-promoting agent according to [1], which is added to a culture medium of pluripotent stem cells in an amount of 0.01 to 10 mM in terms of β-nicotinamide mononucleotide.

[3] The pluripotent stem cell differentiation-promoting agent of [1] or [2], which is used to obtain differentiated cells from one or more pluripotent stem cells selected from the group consisting of embryonic stem cells, artificial pluripotent stem cells, mesenchymal stem cells, hematopoietic stem cells, neural stem cells, and skin stem cells.

[4] A method for differentiating pluripotent stem cells, comprising culturing pluripotent stem cells in a culture medium containing a β-nicotinamide mononucleotide or a pharmacologically acceptable salt thereof, and a solvate thereof.

[5] The method according to [4], wherein the β-nicotinamide mononucleotide concentration of the culture medium is 0.01 to 10 mM.

[6] The method according to [4] or [5], wherein the culture medium is a differentiation-inducing culture medium containing one or more differentiation-inducing factors that differentiate the pluripotent stem cells.

[7] The method according to [6], wherein the differentiation-inducing culture medium is a culture medium for differentiating pluripotent stem cells into either endoderm, mesoderm or ectoderm.

[8] The method according to [4] or [5], wherein the pluripotent stem cells are cultured in a culture medium maintaining pluripotency and containing a β-nicotinamide mononucleotide or a pharmacologically acceptable salt thereof, and a solvate thereof, and are thereafter cultured in a differentiation-inducing culture medium containing one or more differentiation-inducing factors.

[9] The method according to any one of [4] to [8], wherein the pluripotent stern cells are one or more selected from the group consisting of embryonic stem cells, artificial pluripotent stern cells, mesenchymal stem cells, hematopoietic stem cells, neural stem cells, and skin stem cells.

[10] A method for promoting differentiation of pluripotent stem cells, comprising culturing pluripotent stem cells in a culture medium containing a β-nicotinamide mononucleotide or a pharmacologically acceptable salt thereof, and a solvate thereof.

Effects of the Invention

The pluripotent stem cell differentiation-promoting agent according to the present invention can promote differentiation of pluripotent stem cells into differentiated cells by acting on pluripotent stem cells such as iPS cells and ES cells. Therefore, more differentiated cells can be efficiently prepared by culturing the pluripotent stern cells in a culture medium containing the pluripotent stem cell differentiation-promoting agent.

BEST MODE FOR CARRYING OUT THE INVENTION

Figure 1:
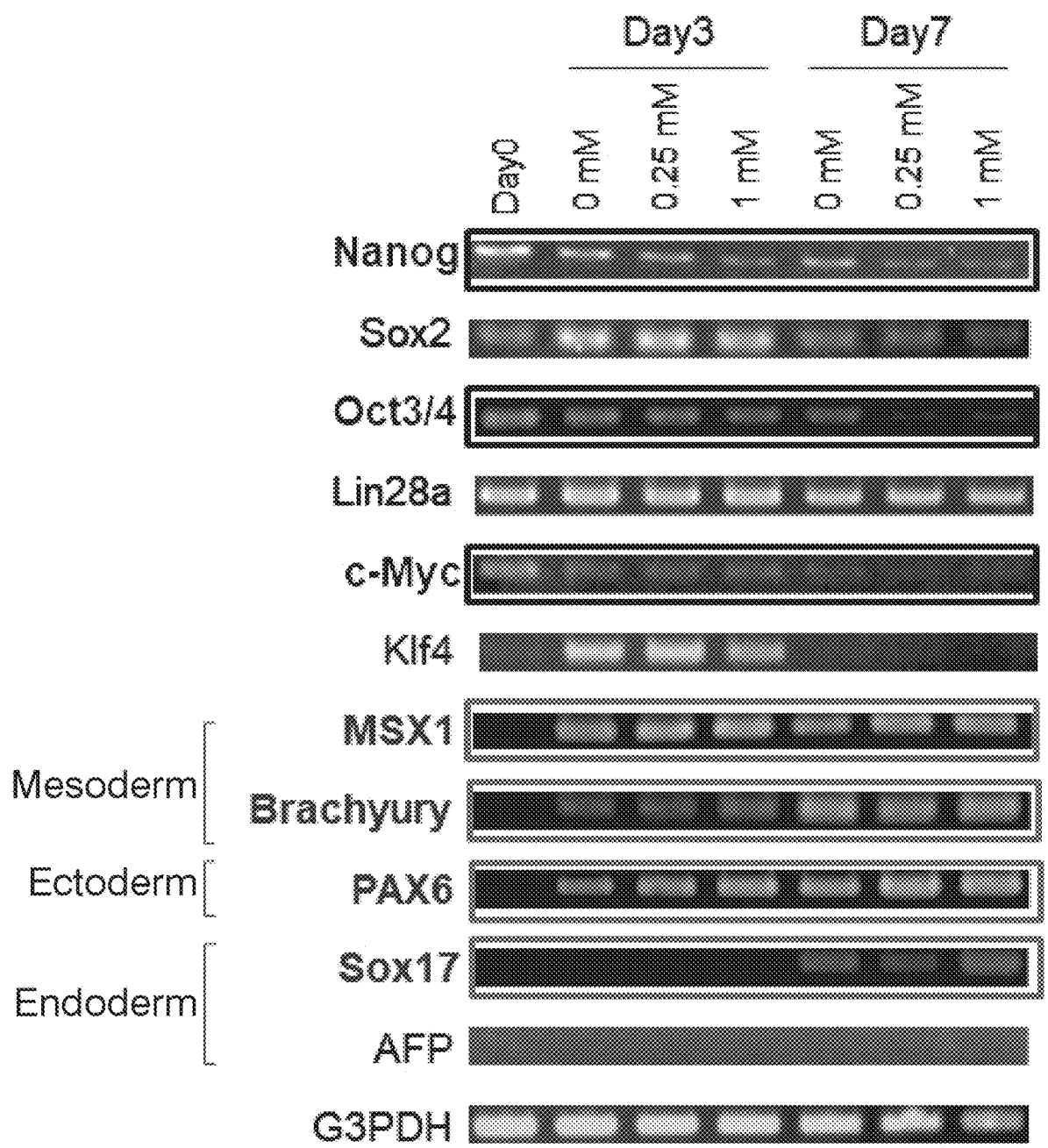
FIG. 1 is a diagram showing the results of RT-PCR for the expression level of each marker in the iPS cells cultured in a differentiation-inducing culture medium supplemented with the β-NMN in Example 1.

In the present invention and the specification of the present application, pluripotent stem cells are undifferentiated cells having self-renewal ability and pluripotency (ability to differentiate into various cell types), and examples thereof include somatic stem cells such as mesenchymal stem cells, hematopoietic stem cells, neural stem cells, skin stern cells or the like, in addition to pluripotent stern cells such as ES cells, iPS cells or the like. Among the examples, pluripotent stem cells capable of differentiating into any of ectoderm cells, mesoderm cells, and endoderm cells are preferred.

In the present invention and the specification of the present application, "promoting differentiation of pluripotent stem cells" means increasing the amount of differentiated cells obtained when the pluripotent stem cells are differentiation-induced. Specifically, to promote the differentiation of pluripotent stein cells, there are an aspect of improving the differentiation efficiency of the pluripotent stem cells, an aspect of promoting cell proliferation during the induction of differentiation, and an aspect of improving the differentiation efficiency of the pluripotent stem cells and promoting the cell proliferation during the differentiation-induction.

The pluripotent stem cell differentiation-promoting agent according to the present invention (hereinafter, may be referred to as "differentiation-promoting agent of the present invention") contains NMN (chemical formula: $C_{11}H_{15}N_2O_8P$) as an active ingredient and is added to the culture medium when the pluripotent stem cells are differentiated. NMN can improve the differentiation efficiency of the pluripotent stem cells into various germ layer cells and somatic cells, and can enhance the proliferative property of the differentiated somatic cells. Therefore, by differentiating the pluripotent stem cells in the presence of NMN, the differentiated cells can be more efficiently obtained from the pluripotent stem cells.

Regarding NMN, there are two types of α and β as optical isomers, but NMN, which is used as the active ingredient of the differentiation-promoting agent of the present invention, is β-NMN (CAS number: 1094-61-7). A structure of β-NMN is shown below.

[Chemical formula 1]

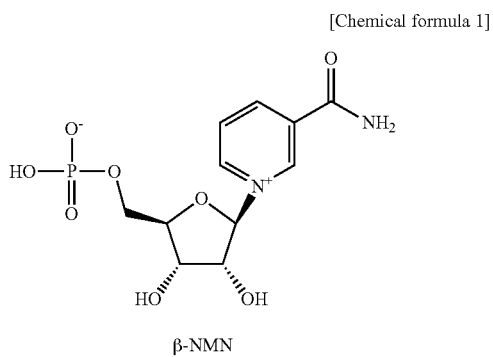 [SMILES: NC(=O)c1ccc[n+]([C@@H]2O[C@H](COP(=O)([O-])O)[C@@H](O)[C@H]2O)c1]

β-NMN

β-NMN as an active ingredient may be prepared by any method. For example, β-NMN obtained by purifying β-NMN artificially synthesized by a chemical synthesis method, an enzymatic method, a fermentation method, or the like can be used as the active ingredient. In addition, because β-NMN is a component widely present in a living body, β-NMN obtained by extraction and purification from natural raw materials such as animals, plants, and microorganisms can also be used as the active ingredient. Furthermore, commercially available purified β-NMN may be used.

As a chemical synthesis method for synthesizing β-NMN, for example, β-NMN can be produced by reacting NAM with L-ribose tetraacetate, and phosphorylating the obtained nicotinamide mononucleotide. In addition, as an enzymatic method, for example, β-NMN can be produced from NAM and 5'-phosphoribosyl-1'-pyrophosphate (PRPP) by nicotinamide phosphoribosyltransferase (NAMPT). As a fermentation method, for example, β-NMN can be produced from NAM using a metabolic system of a microorganism expressing NAMPT.

The active ingredient of the differentiation-promoting agent of the present invention may be a pharmaceutically acceptable salt of β-NMN. The pharmaceutically acceptable salt of β-NMN may be an inorganic acid salt or an organic acid salt having a basic site such as an amine. Examples of acids constituting such acid salts include acetic acid, benzenesulfonic acid, benzoic acid, camphorsulfonic acid, citric acid, ethenesulfonic acid, fumaric acid, gluconic acid, glutamic acid, hydrobromic acid, hydrochloric acid, isethionic acids, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid, p-toluenesulfonic acid, and the like. In addition, the pharmaceutically acceptable salt of β-NMN may be an alkali salt or an organic salt having an acidic site such as a carboxylic acid. Examples of bases constituting such acid salts include bases which are alkali metal salts or alkaline earth metal salts and which are induced from bases such as sodium hydride, potassium hydroxide, calcium hydroxide, aluminum hydroxide, lithium hydroxide, magnesium hydroxide, zinc hydroxide, ammonia, trimethyl ammonia, triethyl ammonia, ethylene diamine, lysine, arginine, ornithine, choline, N,N'-dibenzyl ethylenediamine, chloroprocaine, procaine, diethanolamine, N-benzylphenethylamine, diethylamine, piperazine, tris(hydroxymethyl)-aminomethane, and tetramethyl ammonium hydroxide.

The active ingredient of the differentiation-promoting agent of the present invention may be a pharmaceutically acceptable salt or solvate of free β-NMN. Examples of solvents that form the above-mentioned solvate include water, ethanol, and the like.

The differentiation-promoting agent of the present invention may contain other active ingredients in addition to β-NMN. Said other active ingredients used in combination with β-NMN may be used alone or in combination of two or more. Examples of said other active ingredients include components known to enhance the survival efficiency and proliferation efficiency of the pluripotent stem cells such as albumin, ascorbic acid, α-tocopherol, insulin, transferrin, sodium selenite, ethanolamine, Rock inhibitor or the like, components known to enhance the differentiation efficiency of the pluripotent stem cells such as valproic acid, dimethyl sulfoxide, dexamethasone, butyric acid, trichostatin A, GSK3 inhibitor, BMP inhibitor, Wnt inhibitor, activin, noggin or the like, and the like, and can be appropriately selected and used.

When the pluripotent stem cells are induced to differentiate, the differentiation-inducing culture medium may contain the differentiation-promoting agent of the present invention to promote the differentiation of the pluripotent stem cells. Further, the differentiation of the pluripotent stem cells can also be promoted by culturing them in an undifferentiated cell culture medium containing the differentiation-promoting agent of the present invention prior to differentiation-induction, and then culturing them in a differentiation-inducing culture medium not containing the differentiation-promoting agent of the present invention.

The amount of the differentiation-promoting agent of the present invention added to the differentiation-inducing culture medium or the undifferentiated cell culture medium is not particularly limited as long as it has a concentration sufficient to increase the amount of the differentiated cells obtained by differentiation-inducing the pluripotent stem cells as compared to the case of culturing in a culture medium not containing the differentiation-promoting agent, and the amount of the differentiation-promoting agent can be appropriately adjusted in consideration of the type of the pluripotent stem cells, type of the objective differentiated cells, addition timing to the culture medium, balance with other components of the culture medium, and the like. If the β-NMN concentration in the culture medium is too low, the effect of promoting the differentiation of the pluripotent stem cells may be weak. When β-NMN is contained in the culture medium in an excessive amount, there is a possibility that the differentiation-induction or the cell growth during the differentiation-induction may be suppressed. The content of the differentiation-promoting agent of the present invention in the culture medium is preferably such that the β-NMN concentration is 0.01 to 10 mM, more preferably 0.05 to 5 mM, and even more preferably 0.1 to 1 mM. When the β-NMN concentration is within the above range, differentiation of the pluripotent stem cells can be sufficiently promoted.

Culturing of the pluripotent stem cells in the presence of the differentiation-promoting agent of the present invention can be performed by a conventional method except that the differentiation-inducing culture medium or the undifferentiated cell culture medium contains the differentiation-promoting agent of the present invention. For example, the culture conditions can be generally those for culturing animal cells, and may be appropriately modified as necessary. For example, the culture can be performed at a culture temperature of 30 to 40° C., a $CO_2$ concentration of 1 to 10% by volume, and an $O_2$ concentration of 0.1 to 25% by volume.

The undifferentiated cell culture medium containing the differentiation-promoting agent of the present invention is, for example, generally used for culture mediums for maintaining or proliferating the pluripotent stem cells, or for culturing animal cells. In addition, commercially available culture medium for various pluripotent stem cells can also be used. Specific examples of the culture media for undifferentiated cells containing the differentiation-promoting agent of the present invention include Eagle's minimum essential medium (MEM), Dulbecco's Modified Eagle Medium (DMEM), α-Eagle minimum essential medium (α-MEM), lscove Modified Dulbecco's Medium (IMDM), F-12 medium, F-10 medium, DMEM/F12 medium, RPM1-1640 medium, mesenchymal cell basal medium (MSCBM), E8 (Essential 8) medium, TeSR-E8 medium, mTeSR1 medium and the like. if necessary, amino acids, inorganic salts, vitamins, antibiotics and the like may be added to these media. These culture media may appropriately contain components known to enhance the survival efficiency and proliferation efficiency of the pluripotent stem cells, components known to have the action of maintaining the undifferentiated state of the pluripotent stem cells, and the like. Examples of the components that enhance the survival efficiency of pluripotent stem cells include Rho kinase (ROCK) inhibitors.

As the differentiation-inducing culture medium containing the differentiation-promoting agent of the present invention, a culture medium containing one or more differentiation-inducing factors in a culture medium containing nutrients necessary for cell survival can be used. Examples of the culture medium containing the nutrients necessary for cell survival include the above-mentioned culture medium for undifferentiated cells. The differentiation-inducing factor to be contained in the culture medium for undifferentiated cells can be appropriately determined from among a wide variety of the differentiation-inducing factors described in various documents in consideration of the type of pluripotent stem cells to be used, type of the objective differentiated cells, and the like. In addition, a commercially available differentiation-inducing culture medium such as E6 (Essential 6) medium can also be used. In addition to the differentiation-promoting agent of the present invention, these culture media may appropriately contain components known to enhance the survival efficiency and proliferation efficiency of the pluripotent stem cells, components known to have the action of promoting the differentiation of pluripotent stem cells, and the like.

The pluripotent stem cells whose differentiation is promoted by the differentiation-promoting agent of the present invention are preferably animal-derived pluripotent stem cells, more preferably mammalian-derived pluripotent stem cells, and more preferably human-derived pluripotent stem cells. The pluripotent stem cells whose differentiation is promoted by the differentiation-promoting agent of the present invention are preferably animal-derived ES cells, iPS cells, or mesenchymal stem cells, more preferably mammalian-derived ES cells, iPS, or mesenchymal stem cells, and even more preferably human-derived ES cells, iPS cells, or mesenchymal stem cells.

Particularly, the differentiation-promoting agent of the present invention is preferably used for promoting the differentiation of the pluripotent stem cells capable of differentiating into any cells of ectoderm, mesoderm, and endoderm, and particularly preferably used for promoting the differentiation of ES cells or iPS cells into any one of the germ layers. For example, by culturing the ES cells or iPS cells in a differentiation-inducing culture medium containing one or more differentiation-inducing factors that differentiate these pluripotent stem cells into any one of the three germ layers and the differentiation-promoting agent of the present invention, differentiation into desired germ layer cells can be promoted.

EXAMPLE

Next, the present invention will be described in more detail with reference to examples, but the present invention is not limited to the following examples.

In the following experiments, as the culture medium for iPS cells, a medium prepared by adjusting DMEM/F12 medium to contain 19.4 mg/L of insulin, 10.7 mg/L of transferrin, 64 mg/L of ascorbic acid, 14 μg/L of sodium selenite, 100 μg/L of human FGF2, 2 μg/L of human TGFβ1, 543 mg/L of sodium hydrogen carbonate, was used.

Example 1

The effect of β-NMN on the differentiation of three germ layers of the iPS cells was examined. As the iPS cells, the human iPS cell strain 201B7 was used.
<Culture>
A U-bottom shape 96-well plate "Nunclon Sphera 96 U-well plate" (manufactured by Thermo Fisher Scientific) was seeded with iPS cells at 10,000 cells/well, and cultured in an E6 culture medium (manufactured by Gibco) as a differentiation-inducing culture medium adjusted to have a final concentration of β-NMN of 0, 0.25 or 1 mM, and a final concentration of Rock inhibitor of 10 μM for 1 day. The Rock inhibitor was added to suppress Rho-dependent apoptosis. On the 1st and 5th days after seeding, the culture medium was replaced with a culture medium obtained by removing the Rock inhibitor from the culture medium at the time of seeding.
<Measurement of Expression Level of Each Marker by RT-PCR>
Cells on the 3rd and 7th days after seeding were sampled and subjected to RT-PCR to investigate the expression levels of undifferentiated markers (Nanog, Sox2, Oct3/4, Lin28a, Klf4), endoderm markers (Sox17, AFP), mesoderm markers (MSX1, Brachyury) and ectodermal markers (PAX6). Specifically, RNA is extracted from the sampled cells using an RNA extraction kit "RNeasy Mini Kit" (manufactured by QIAGEN), and the extracted RNA was used as a template to synthesize cDNA using a reverse transcription kit "Super- Script (registered trademark) III First-Strand Synthesis System" (manufactured by Thermo Scientific). The expression level of each marker was evaluated by PCR using the obtained cDNA. G3PDH was used as a control as an internal standard gene.

The results of staining the PCR products after electrophoresis and separation are shown in FIG. 1. In the figure, "Day 0" shows the results of cells immediately before seeding, and "Day 3" and "Day 7" show the results of the cells of the 3rd and 7th day after seeding, respectively. From this result, it was found that the expression level of each undifferentiated marker was decreased and the expression level of the differentiated marker was increased in the cells differentiation-induced in the presence of β-NMN compared to the cells cultured in the absence of β-NMN.

Example 2

Figure 2:
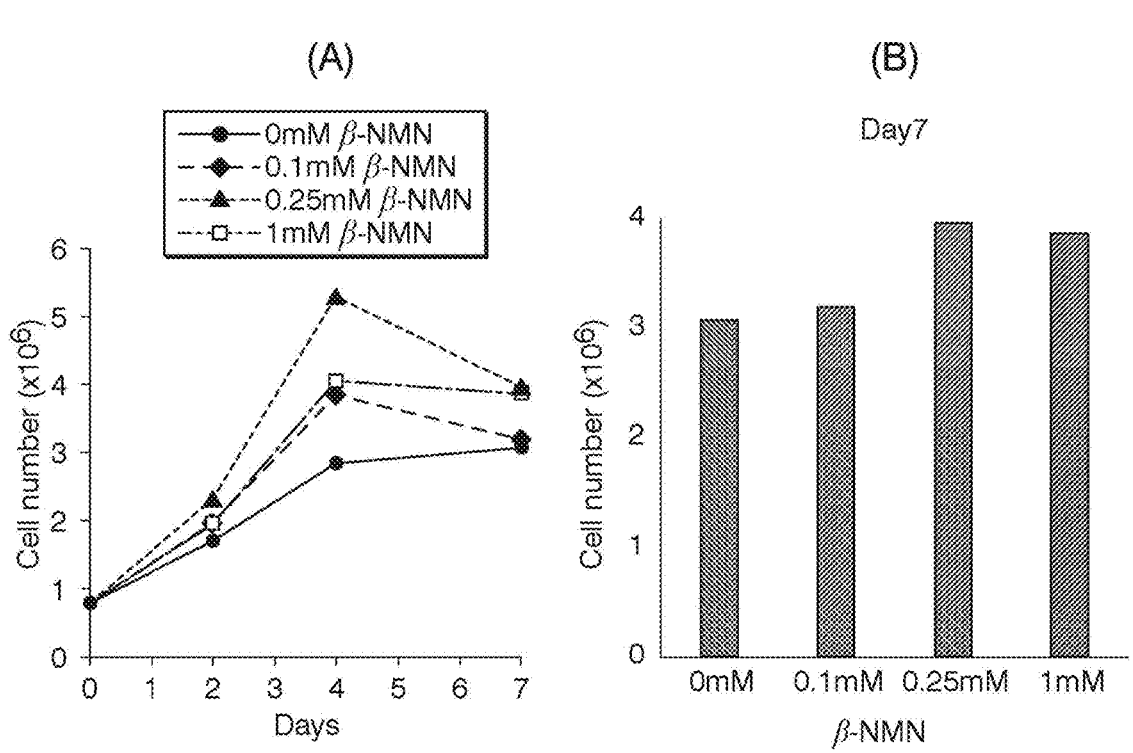
FIG. 2(A) is a diagram showing the time-dependent change of the number of the iPS cells cultured in an ectodermal differentiation-inducing culture medium supplemented with the β-NMN in Example 2.
FIG. 2(B) is a diagram showing the cell numbers of the 7th day after seeding of the iPS cells cultured in ectodermal differentiation-inducing culture medium supplemented with the β-NMN added in Example 2.

The effect of β-NMN on the ectodermal differentiation-induction of the iPS cells was examined. The 201B7 strain was used as the iPS cells.
<Culture>
The iPS cells were seeded in a 12-well plate coated with Matrigel (manufactured by Corning Incorporated) according to the manufacturer's protocol at $8 \times 10^5$ cells/well. The cells in the 12-well plate were cultured in a culture medium prepared by adjusting an ectodermal differentiation-inducing culture medium of "STEMdiff Trilineage Differentiation kit" (manufactured by STEMCELL Technologies) to have a final concentration of β-NMN of 0, 0.1, 0.25, or 1 mM, and a final concentration of Rock inhibitor of 10 μM for 1 day. From the 1st day after seeding, the medium was replaced every day with a culture medium obtained by removing the Rock inhibitor from the culture medium at the time of seeding.
<Time-Dependent Change in Cell Number>
Cells of the 2nd, 4th or 7th day after seeding were sampled and the cell numbers were counted. The time-dependent change in cell number of each sample is shown in FIG. 2(A), and the cell numbers of the 7th day after seeding are shown in FIG. 2(B). As a result, the number of cells cultured in the ectoderm differentiation-inducing culture medium containing β-NMN was larger than the number of cells cultured in the medium not containing β-NMN. From this result, it was found that β-NMN improves the cell proliferative property during the differentiation-induction into ectoderm.
<Measurement of Cells Expressing Ectodermal Differentiation Marker Using Flow Cytometer>
The cells sampled on the 2nd, 4the or 7th day after seeding were fixed with paraformaldehyde and then permeabilized with saponin-containing PBS. Then, the cells were stained with a fluorescence-labeled anti-Nestin antibody (manufactured by Biolegend, clone 10C2) and a fluorescence-labeled anti-Pax6 antibody (manufactured by Becton, Dickinson and Company, clone O18-1330). After washing the stained cells, a flow cytometer "FACScaliber" (manufactured by Becton, Dickinson and Company) was used to analyze the fluorescence intensity of the anti-Nestin antibody and the fluorescence intensity of the anti-Pax6 antibody in each sample. Nestin and Pax6 are the ectodermal differentiation markers.

Figure 3:
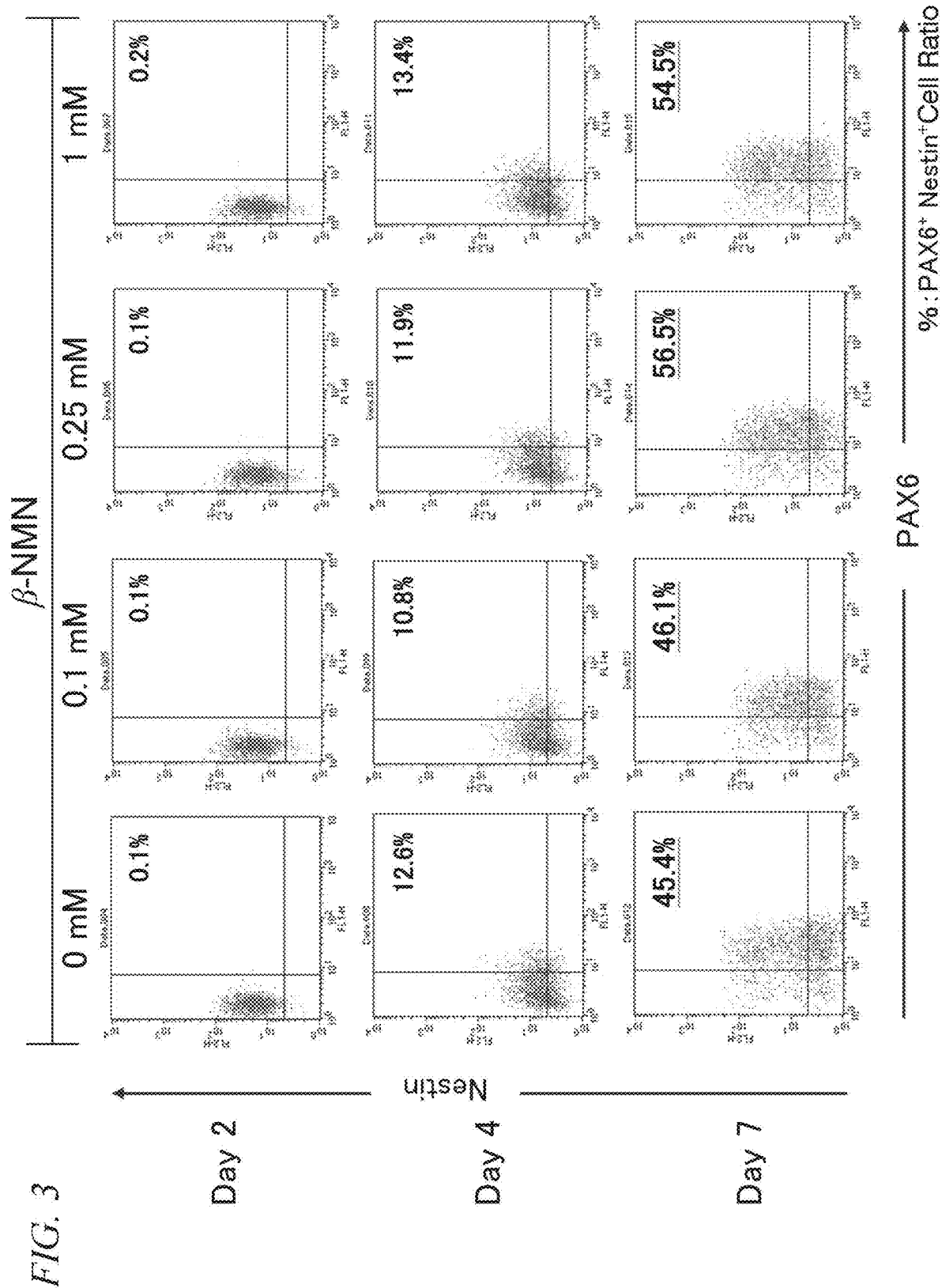
FIG. 3 is a diagram showing the results of fractionating the iPS cells cultured in an ectodermal differentiation-inducing culture medium supplemented with β-NMN by the expression levels of Nestin and Pax6 in Example 2.

The results of fractionating each sample by the expression level of Nestin and Pax6 using a flow cytometer are shown in FIG. 3. The Nestin-positive and Pax6-positive cells are the cells differentiated into ectoderm. The percentage in the figure indicates the ratio (%) of the Nestin-positive Pax6-positive cells to the total amount of cells. As a result, the cells cultured in the presence of β-NMN had a higher ratio of Nestin-positive Pax6-positive cells. That is, it was confirmed that the differentiation efficiency in the ectodermal differentiation can be improved by addition of β-NMN.

From these results, it was found that β-NMN promotes the differentiation of iPS cells into ectodermal cells by improving both the proliferative properties and the differentiation efficiency of the cells during the ectodermal differentiation-induction.

Example 3

Figure 4:
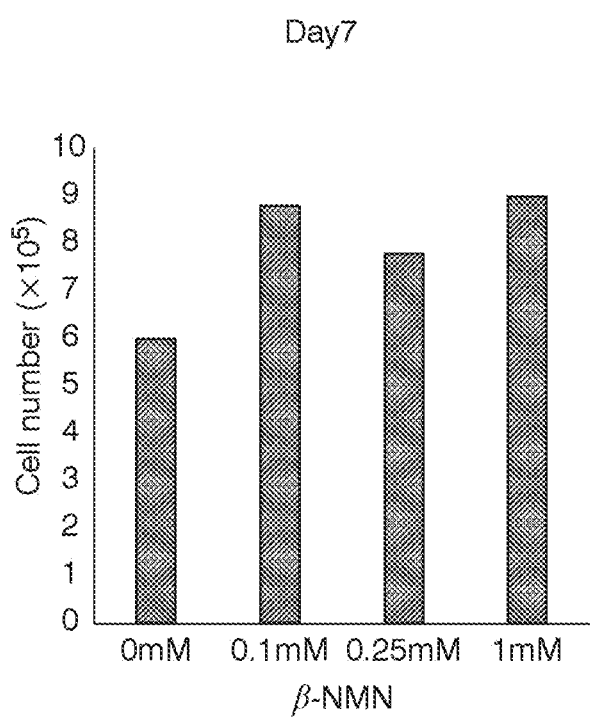
FIG. 4 is a diagram showing the cell numbers of the 7th day after seeding of the iPS cells cultured in a mesodermal differentiation-inducing culture medium supplemented with the β-NMN in Example 3.

The effects of β-NMN on the mesodermal differentiation-induction of iPS cells were examined. The 201B7 strain was used as the iPS cells.
<Culture>
The iPS cells were seeded in a 24-well plate coated with Matrigel (manufactured by Corning Incorporated) according to the manufacturer's protocol at $1 \times 10^5$ cells/well. The cells in the 24-well plate were cultured in a culture medium for iPS cells adjusted to have a final concentration of Rock inhibitor of 10 μM for 1 day. From the 1st day after seeding, the culture medium was replaced with a culture medium prepared by adjusting a mesoderm differentiation-inducing culture medium of "STEMdiff Trilineage Differentiation kit" (manufactured by STEMCELL Technologies) to have a final concentration of β-NMN of 0, 0.1, 0.25, or 1 mM for 1 day. The culture medium was replaced with a culture medium prepared by adjusting a mesodermal differentiation-inducing culture medium to have final concentrations of both β-NMN and Rock inhibitor of 10 μM only on the 1st day after seeding.
<Time-Dependent Change in Cell Number>
Cells of the 7th day after seeding were sampled and the cell numbers were counted. The cell number of each sample on the 7th day after seeding is shown in FIG. 4. As a result, the number of the cells cultured in the mesodermal differentiation-inducing culture medium containing β-NMN was larger than the number of the cells cultured in the medium not containing β-NMN. From this result, it was found that β-NMN improves the cell proliferative property during the differentiation-induction into mesoderm.
<Measurement of Cells Expressing Mesodermal Differentiation Marker Using Flow Cytometer>
The cells sampled on the 5th or 7th day after seeding were fixed with paraformaldehyde and then permeabilized with saponin-containing PBS. Then, the cells were stained with a fluorescence-labeled anti-Brachyury antibody (manufactured by Merck, clone 3E4.2) and a fluorescence-labeled anti-CD56 antibody (manufactured by Biolegend, clone HCD56). After washing the stained cells, a flow cytometer "FACS caliber" (manufactured by Becton, Dickinson and Company) was used to analyze the fluorescence intensity of the anti-Brachyury antibody and the fluorescence intensity of the anti-CD56 antibody in each sample. Brachyury and CD56 are the mesodermal differentiation markers.

Figure 5:
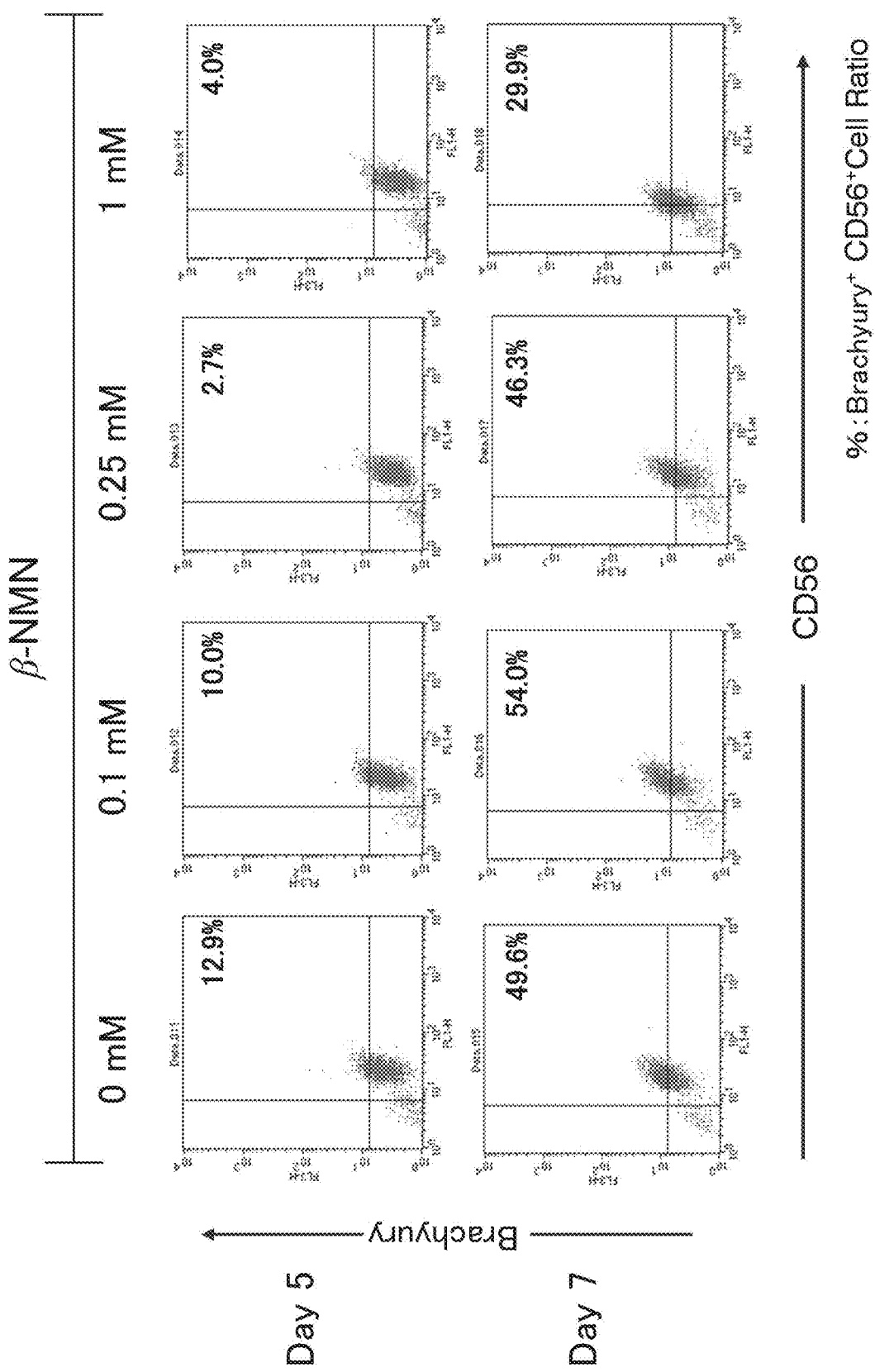
FIG. 5 is a diagram showing the results of fractionating the iPS cells cultured in a mesodermal differentiation-inducing culture medium supplemented with β-NMN by the expression levels of Brachyury and CD56 in Example 3.

The results of fractionating each sample by the expression level of Brachyury and CD56 using a flow cytometer are shown in FIG. 5. The Brachyury-positive and CD56-positive cells are the cells differentiated into mesoderm. The percentages in the figure indicate the ratio (%) of the Brachyury-positive CD56-positive cells to the total amount of cells. As a result, there was no clear difference in the ratio of Brachyury-positive CD56-positive cells between the cells cultured in the presence of β-NMN and the cells cultured in the absence of β-NMN. Particularly, in the cells to which β-NMN was added at 1 mM, the ratio of Brachyury-positive CD56-positive cells was obviously lower than that in the case of culturing without β-NMN. That is, it was confirmed that the addition of β-NMN did not significantly affect the differentiation efficiency in the mesodermal differentiation.

These results show that β-NMN improves the proliferation of the cells upon induction of differentiation into mesodermal cells, but there was no clear difference in differentiation from iPS cells into mesodermal cells.

Example 4

The effects of β-NMN on the induction of endodermal differentiation of iPS cells were examined. As the iPS cells, the 253G1 strain was used.

<Culture>

The iPS cells were seeded in a 24-well plate coated with Matrigel (manufactured by Corning Incorporated) according to the manufacturer's protocol at $3 \times 10^5$ cells/well. The cells in the 24-well plate were cultured in a culture medium for iPS cells adjusted to have a final concentration of Rock inhibitor of 10 μM for 1 day. From the 1st day after seeding, the culture medium was replaced with a culture medium prepared by adjusting an endoderm differentiation-inducing culture medium of "STEMdiff Trilineage Differentiation kit" (manufactured by STEMCELL Technologies) to have a final concentration of β-NMN of 0, 0.1, 0.25, or 1 mM for 1 day. The culture medium was replaced with a culture medium prepared by adjusting an endodermal differentiation-inducing culture medium to have final concentrations of both β-NMN and Rock inhibitor of 10 μM only on the 1st day after seeding.

<Time-Dependent Change in Cell Number>

Figure 6:
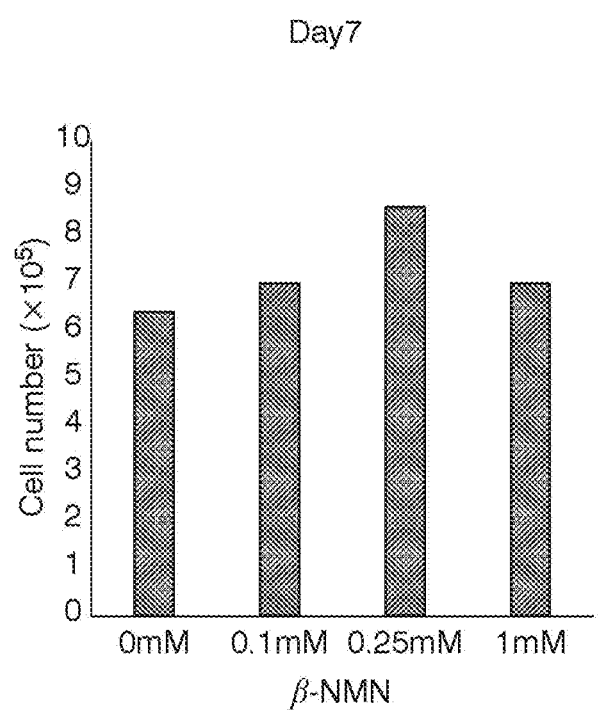
FIG. 6 is a diagram showing the cell numbers of the 7th day after seeding of the iPS cells cultured in an endodermal differentiation-inducing culture medium supplemented with the β-NMN in Example 4.

Cells of the 7th day after seeding were sampled and the cell numbers were counted. The cell number of each sample on the 7th day after seeding is shown in FIG. 6. As a result, the number of the cells cultured in the endodermal differentiation-inducing culture medium containing β-NMN was larger than the number of the cells cultured in the medium not containing β-NMN. From this result, it was found that β-NMN improves the cell proliferative property during the differentiation-induction into endoderm.

<Measurement of Cells Expressing Endodermal Differentiation Marker Using Flow Cytometer>

The cells sampled on the 5th or 7th day after seeding were fixed with paraformaldehyde and then permeabilized with saponin-containing PBS. Then, the cells were stained with a fluorescence-labeled anti-Sox17 antibody (manufactured by Becton, Dickinson and Company, clone P7-969) and a fluorescence-labeled anti-CXCR4 antibody (manufactured by Biolegend, clone 12G5). After washing the stained cells, a flow cytometer "FACS caliber" (manufactured by Becton, Dickinson and Company) was used to analyze the fluorescence intensity of the anti-Sox17 antibody and the fluorescence intensity of the anti-CXCR4 antibody in each sample. Sox17 and CXCR4 are the endodermal differentiation markers.

Figure 7:
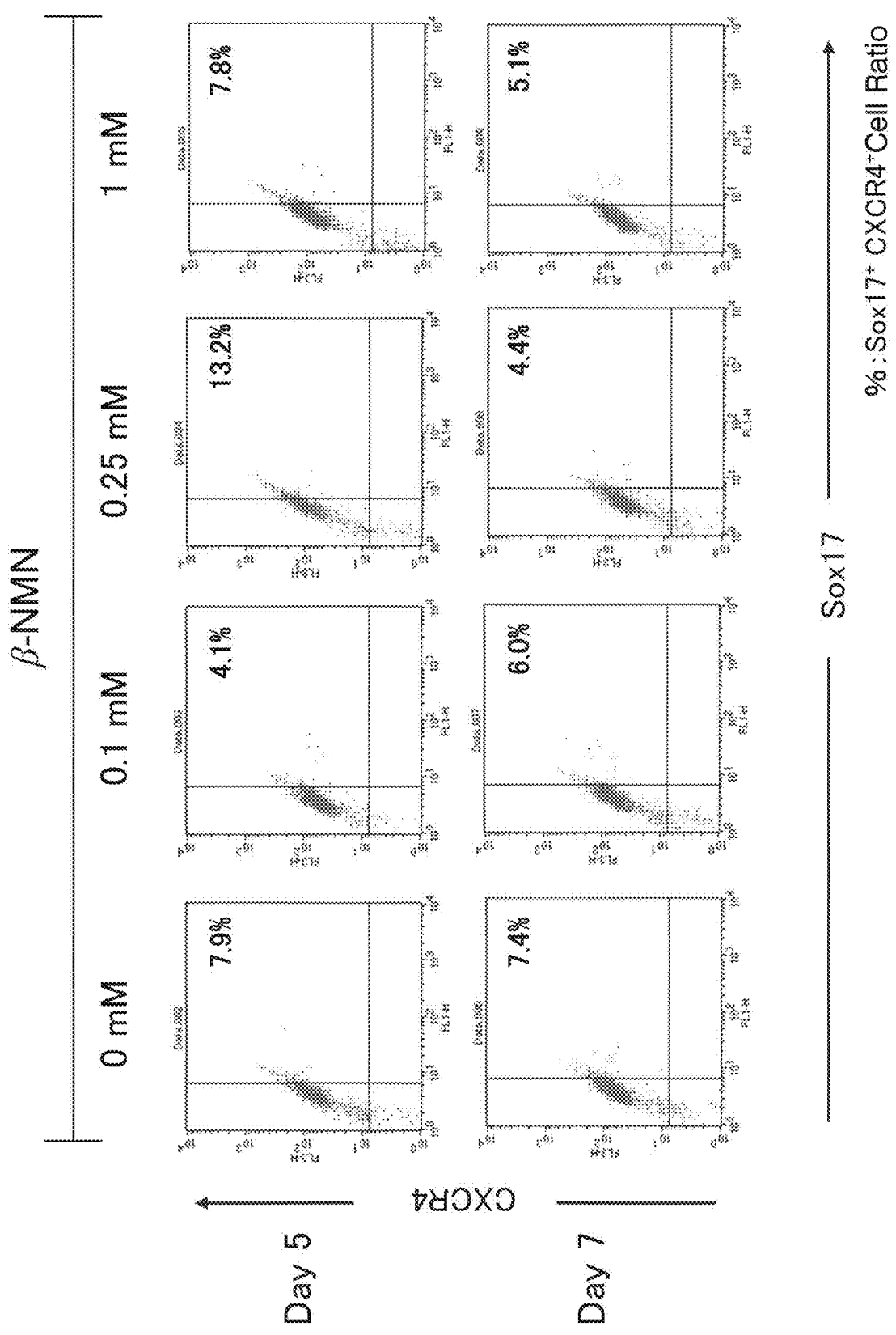
FIG. 7 is a diagram showing the results of fractionating the iPS cells cultured in an endodermal differentiation-inducing culture medium supplemented with β-NMN by the expression levels of Sox17 and CXCR4 in Example 4.

The results of fractionating each sample by the expression level of Sox17 and CXCR4 using a flow cytometer are shown in FIG. 7. The Sox17-positive and CXCR4-positive cells are the cells differentiated into endoderm. The percentages in the figure indicate the ratio (%) of the Sox17-positive CXCR4-positive cells to the total amount of cells. As a result, there was no clear difference in the ratio of Sox17-positive CXCR4-positive cells between the cells cultured in the presence of β-NMN and the cells cultured in the absence of β-NMN. That is, it was confirmed that the addition of β-NMN did not significantly affect the differentiation efficiency in the endodermal differentiation.

From these results, it was found that β-NMN improves the proliferation of cells upon induction of differentiation into endoderm, but there was no clear difference in differentiation from iPS cells into endoderm cells.

Example 5

The effects of culturing in the presence of β-NMN before induction of differentiation on the endodermal differentiation-induction of iPS cells was examined. As the iPS cells, the 253G1 strain was used.

<Culture> iPS cells seeded on a culture dish coated with Matrigel (manufactured by Corning Incorporated) according to the manufacturer's protocol were cultured in a culture medium prepared by adjusting a culture medium for iPS cells to have a final concentration of β-NMN 0, 0.25 or 1 mM, and a final concentration of Rock inhibitor of 10 μM for 1 day. From the 1st day after seeding, the culture medium was replaced every day with a culture medium obtained by removing the Rock inhibitor from the culture medium at the time of seeding. When the confluent reached 70 to 80%, the iPS cells were detached from the culture dish and collected.

The collected iPS cells were seeded at $3 \times 10^5$ cells/well in a 24-well plate coated with Matrigel (manufactured by Corning Incorporated) according to the manufacturer's protocol. The cells in the 24-well plate were cultured for 1 day in a culture medium prepared by removing β-NMN from the culture medium when culturing in the culture dish and adjusting to have a final concentration of Rock inhibitor of 10 μM. From the 1st day after seeding, the medium was replaced every day with a culture medium for endodermal differentiation-induction of "STEMdiff Trilineage Differentiation kit" (manufactured by STEMCELL Technologies).

<Time-Dependent Change in Cell Number>

Figure 8:
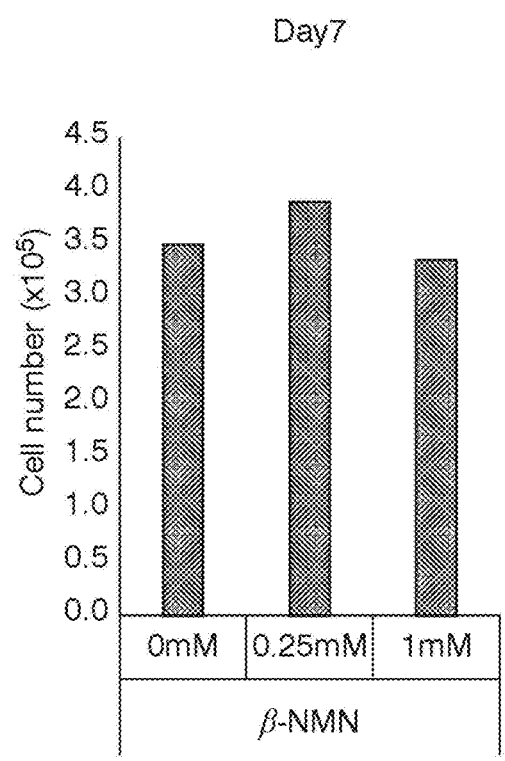
FIG. 8 is a diagram showing the cell numbers of the 7th day after seeding of the endodermal differentiation-induced iPS cells after culturing in a culture medium for iPS cells supplemented with the β-NMN in Example 5.

Cells on the 7th day after seeding were sampled and the numbers of cells were counted. The cell number of each sample on the 7th day after seeding is shown in FIG. 8. As a result, there was no clear difference in cell number between the cells that have undergone endodermal differentiation-induction after being cultured in a culture medium for iPS cells containing β-NMN and the cells that have undergone endodermal differentiation-induction after being cultured in a culture medium for iPS cells not containing β-NMN. That is, it was found that the addition of β-NMN during the undifferentiated culture had little effect on the cell proliferation during the subsequent endoderm differentiation.

<Measurement of Cells Expressing Endodermal Differentiation Marker Using Flow Cytometer>

The cells sampled on the 5th or 7th day after seeding were fixed with paraformaldehyde and then permeabilized with saponin-containing PBS. Then, the cells were stained with a fluorescently labeled anti-Sox17 antibody (manufactured by Becton, Dickinson and Company, clone P7-969) and a fluorescently labeled anti-FoxA2 antibody (manufactured by Becton, Dickinson and Company, clone N17-280). After washing the stained cells, a flow cytometer "FACS caliber" (manufactured by Becton, Dickinson and Company) was used to analyze the fluorescence intensity of the anti-Sox17 antibody and the fluorescence intensity of the anti-FoxA2 antibody in each sample. Sox17 and FoxA2 are the endodermal differentiation markers.

Figure 9:
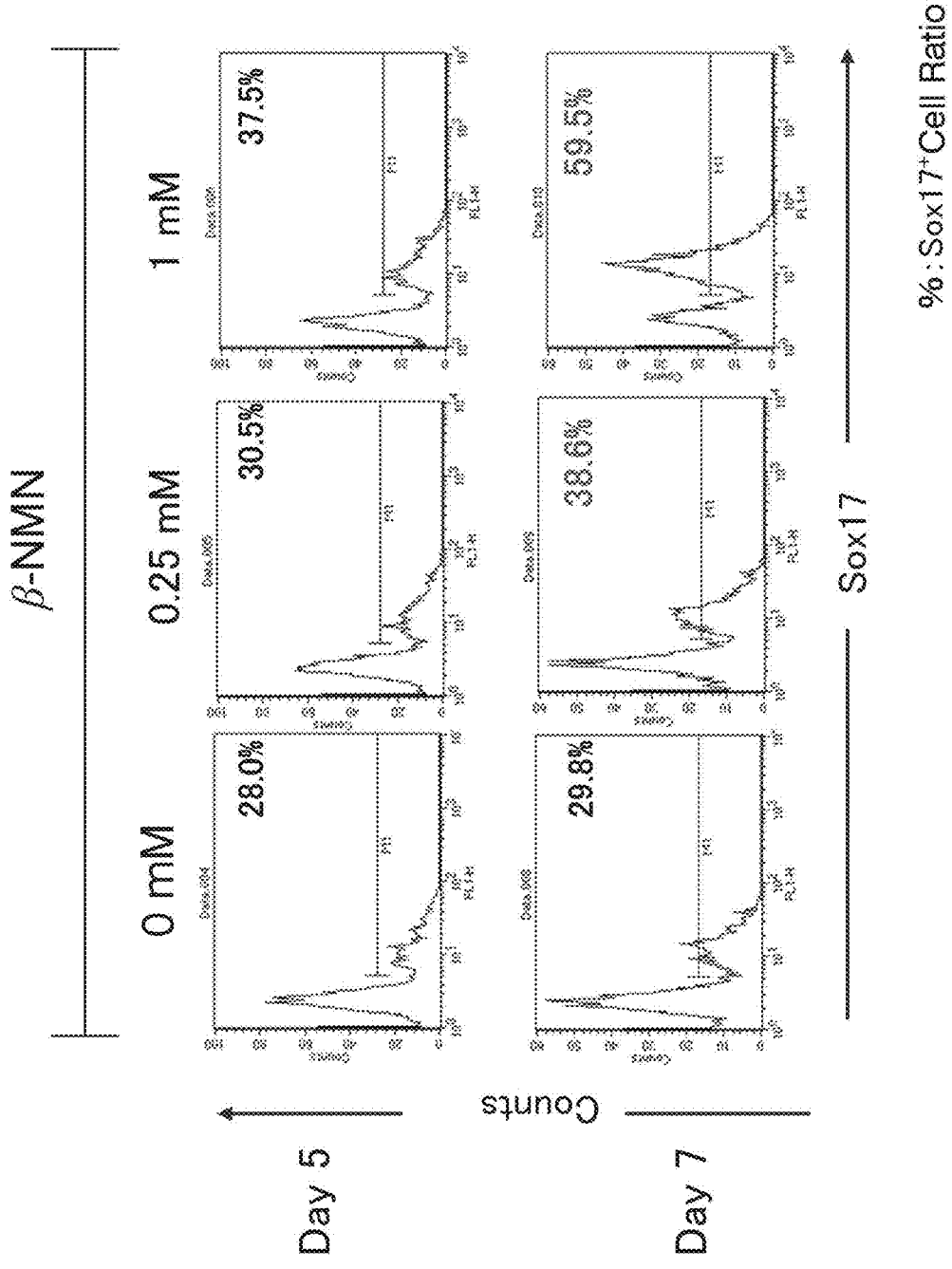
FIG. 9 is a diagram showing the results of fractionating the endodermal differentiation-induced iPS cells after culturing in a culture medium for iPS cells supplemented with β-NMN by the expression level of Sox17 in Example 5.

The results of fractionating each sample by the expression level of Sox17 by a flow cytometer are shown in FIG. 9. The Sox17-positive cells are the cells differentiated into endoderm. The percentage in the figure indicates the ratio (%) of Sox17-positive cells to the total amount of cells. As a result, the ratio of Sox17-positive cells in the iPS cells cultured in the presence of β-NMN during the undifferentiated culture was higher than that in the iPS cells cultured in the absence of β-NMN. That is, it was confirmed that the differentiation efficiency in the endodermal differentiation can be improved by culturing in the presence of β-NMN during the undifferentiated culture.

From these results, it was found that by carrying out the endodermal differentiation-induction of iPS cells after culturing the iPS cells in the presence of β-NMN in advance, the efficiency of endodermal differentiation can be improved, thereby promoting the differentiation of iPS cells into endoderm cells.

Example 6

The effects of culturing in the presence of β-NMN before induction of differentiation on the mesodermal differentiation-induction of iPS cells was examined. As the iPS cells, the 201B7 strain was used.
<Culture>
The iPS cells were cultured in a culture dish in the same manner as in Example 5, and when the confluent reached 70 to 80%, the iPS cells were detached from the culture dish and collected.

Figure 10:
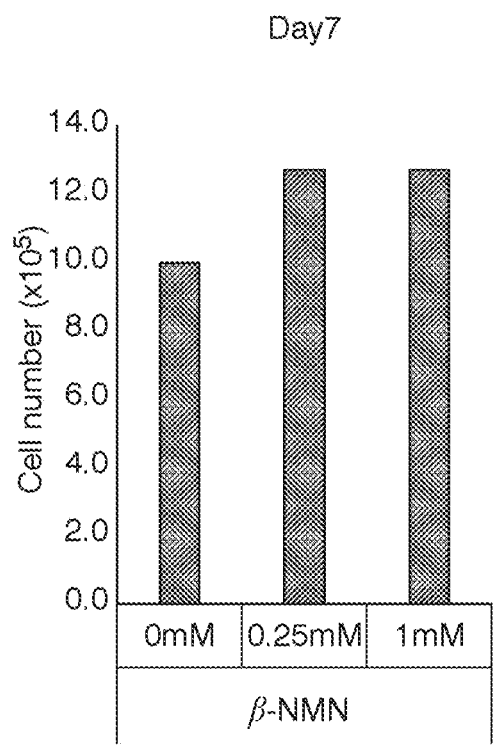
FIG. 10 is a diagram showing the cell numbers of the 7th day after seeding of the mesodermal differentiation-induced iPS cells after culturing in a culture medium for iPS cells supplemented with the β-NMN in Example 6.

The collected iPS cells were seeded at $1 \times 10^5$ cells/well in a 24-well plate coated with Matrigel (manufactured by Corning Incorporated) according to the manufacturer's protocol. The cells in the 24-well plate were cultured for 1 day in a culture medium prepared by removing β-NMN from the culture medium when culturing in the culture dish and adjusting to have a final concentration of Rock inhibitor of 10 μM. From the 1st day after seeding, the medium was replaced every day with a culture medium for mesodermal differentiation-induction of "STEMdiff Trilineage Differentiation kit" (manufactured by STEMCELL Technologies).
<Time-Dependent Change in Cell Number>
The cells of the 7th day after seeding were sampled and the cell numbers were counted. The cell number of each sample on the 7th day after seeding is shown in FIG. 10. As a result, the number of the cells that have undergone mesodermal differentiation-induction after being cultured in a culture medium for iPS cells containing β-NMN was larger than that of the cells that have undergone mesodermal differentiation-induction after being cultured in a culture medium for iPS cells not containing β-NMN. That is, it was found that the addition of β-NMN during the undifferentiated culture improves cell proliferation during the subsequent mesodermal differentiation.
<Measurement of Cells Expressing Mesodermal Differentiation Marker Using Flow Cytometer>
In the same manner as in Example 3, the cells sampled on the 5th or 7th day after seeding were stained with a fluorescently labeled anti-Brachyury antibody and a fluorescently labeled anti-CD56 antibody, and a flow cytometer was used to analyze the fluorescence intensity of the anti-Brachyury antibody and the fluorescence intensity of the anti-CD56 antibody in each sample.

Figure 11:
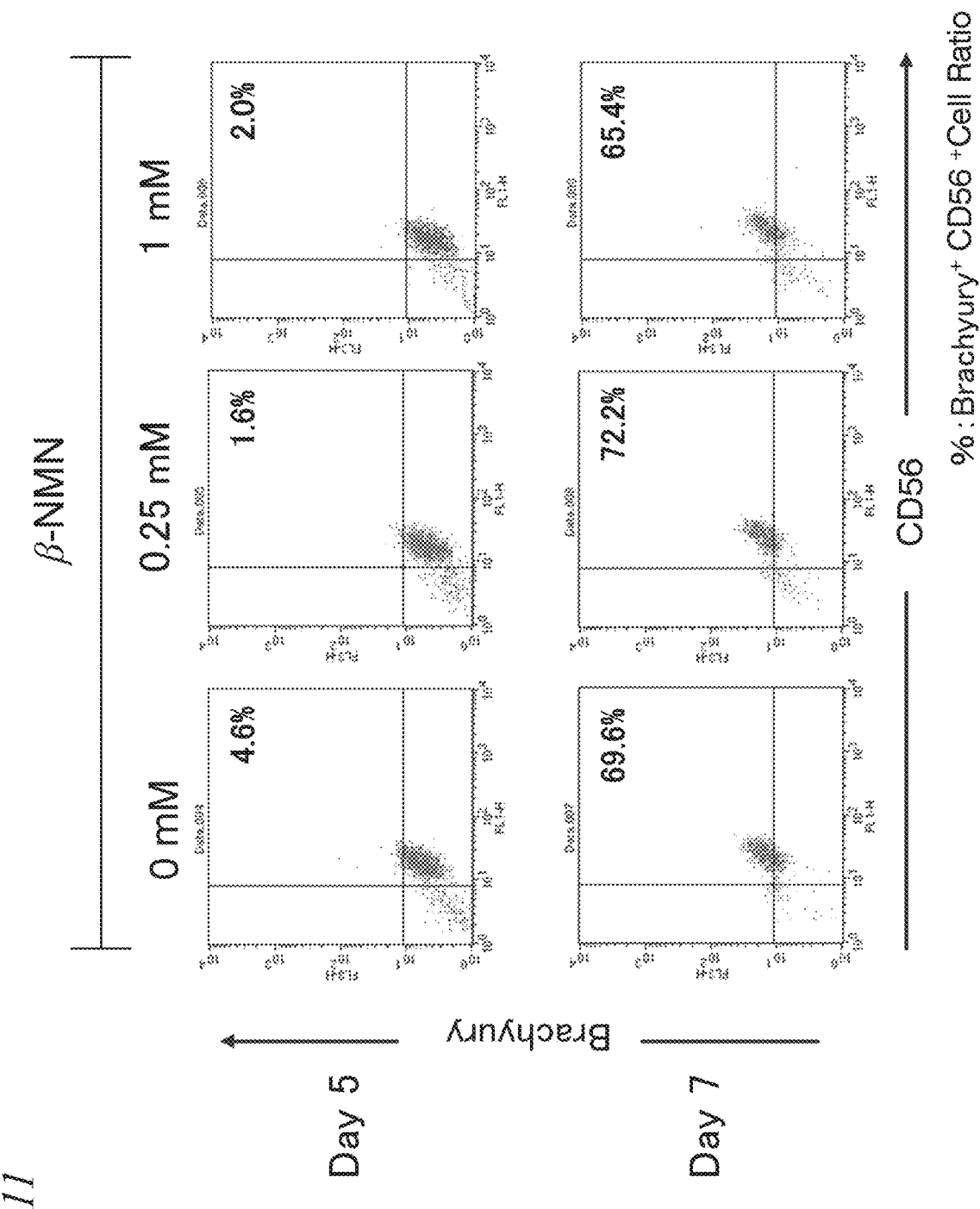
FIG. 11 is a diagram showing the results of fractionating the mesodermal differentiation-induced iPS cells after culturing in a culture medium for iPS cells supplemented with β-NMN by the expression level of Brachyury and CD56 in Example 6.

The results of fractionating each sample by the expression level of Brachyury and CD56 using a flow cytometer are shown in FIG. 11. The Brachyury-positive and CD56-positive cells are the cells differentiated into mesoderm. The percentages in the figure indicate the ratio (%) of Brachyury-positive CD56-positive cells to the total amount of cells. As a result, there was no clear difference in the ratio of Brachyury-positive CD56-positive cells after differentiation-induction between the cells cultured in the presence of β-NMN before mesodermal differentiation-induction and the cells cultured in the absence of β-NMN. That is, it was confirmed that β-NMN at the time of undifferentiated culture did not significantly affect the differentiation efficiency in the subsequent induction of mesodermal differentiation.

As shown in the results, by carrying out the mesodermal differentiation-induction of iPS cells after culturing the iPS cells in the presence of β-NMN in advance, the cell proliferative property at the time of mesodermal differentiation-induction was improved, but there was no clear difference in the differentiation from iPS cells into mesodermal cells.

Example 7

The effects of culturing in the presence of β-NMN before induction of differentiation on the ectodermal differentiation-induction of iPS cells was examined. As the iPS cells, the 201B7 strain was used.
<Culture>
The iPS cells were cultured in a culture dish in the same manner as in Example 5, and when the confluent reached 70 to 80%, the iPS cells were detached from the culture dish and collected.

Figure 12:
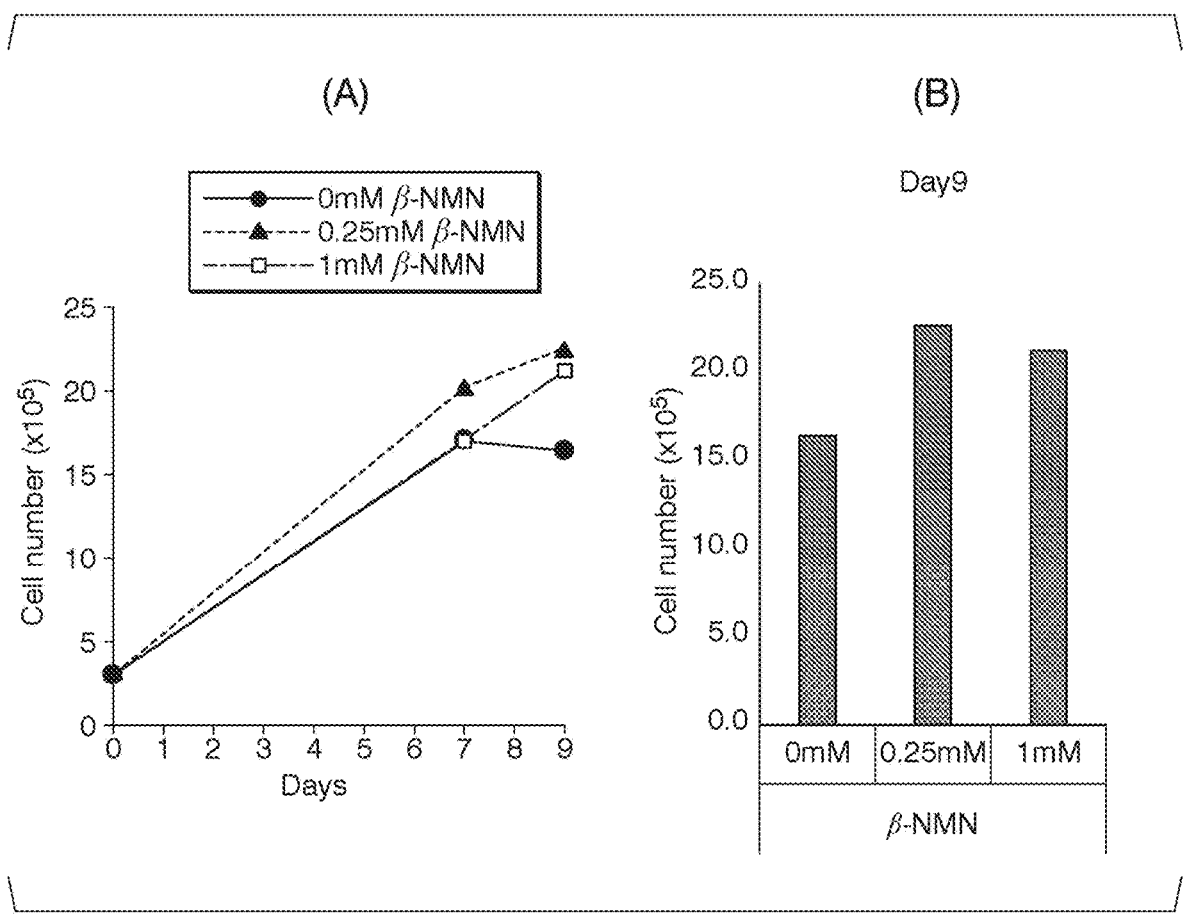
FIG. 12(A) is a diagram showing a time-dependent change in the cell number of the ectodermal differentiation-induced iPS cells after culturing in a culture medium for iPS cells supplemented with the β-NMN in Example 7.
FIG. 12(B) is a diagram showing the cell numbers of the 9th day after seeding of the ectodermal differentiation-induced iPS cells after culturing in a culture medium for iPS cells supplemented with the β-NMN in Example 7.
Figure 13:
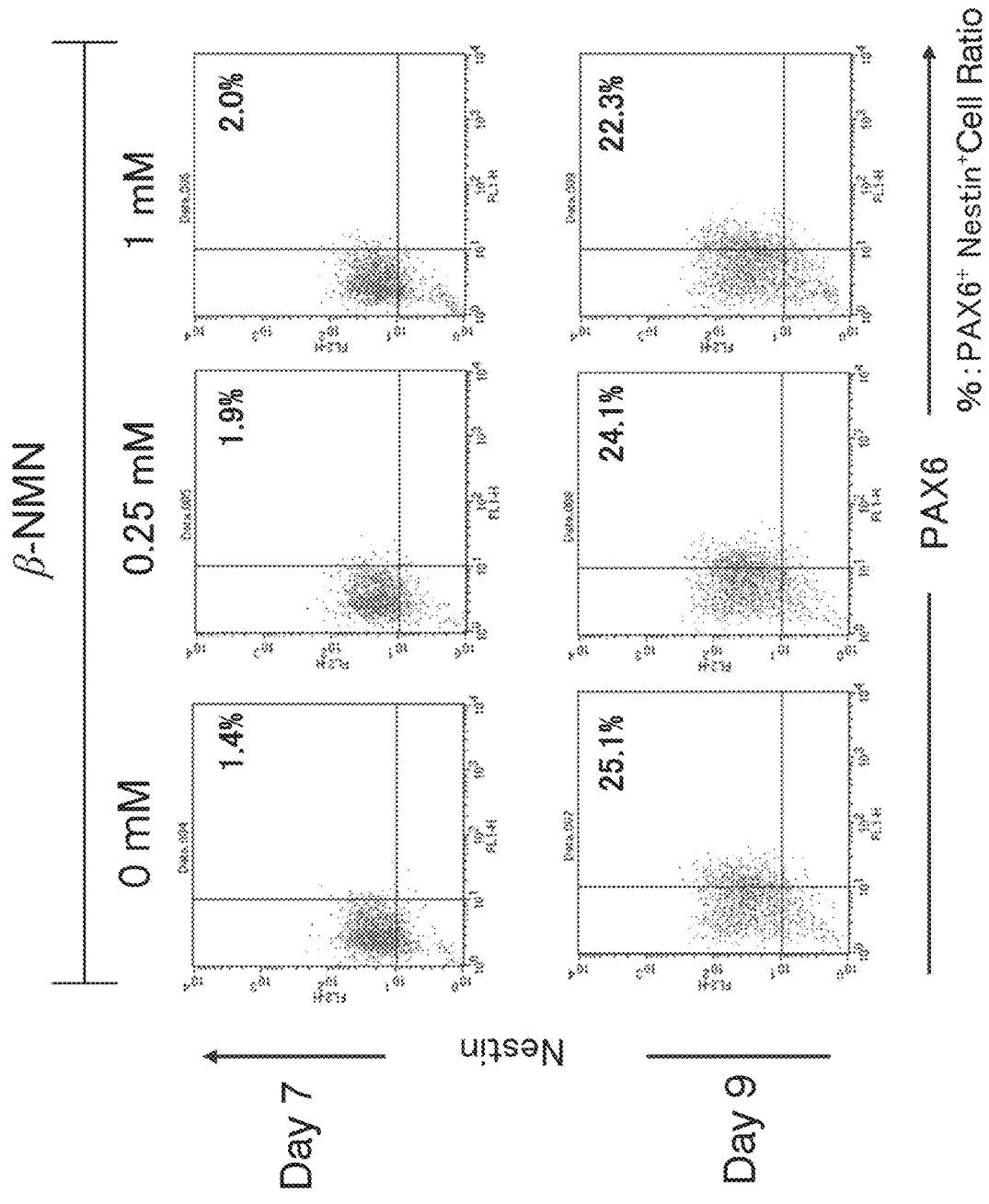
FIG. 13 shows the results of fractionating the ectodermal differentiation-induced iPS cells after culturing in a culture medium for iPS cells supplemented with β-NMN by the expression levels of Nestin and Pax6 in Example 7.

The collected iPS cells were seeded at $3 \times 10^5$ cells/well in a 24-well plate coated with Matrigel (manufactured by Corning Incorporated) according to the manufacturer's protocol. The cells in the 24-well plate were cultured for 1 day in a culture medium prepared by removing β-NMN from the culture medium when culturing in the culture dish and adjusting to have a final concentration of Rock inhibitor of 10 μM. From the 1st day after seeding, the medium was replaced every day with a culture medium for ectodermal differentiation-induction of "STEMdiff Trilineage Differentiation kit" (manufactured by STEMCELL Technologies).
<Time-Dependent Change in Cell Number>
The cells of the 7th or 9th day after seeding were sampled and the cell numbers were counted. The time-dependent change in cell number of each sample is shown in FIG. 12(A), and the cell number of each sample on the 9th day after seeding is shown in FIG. 12(B). As a result, the number of the cells that have undergone ectodermal differentiation-induction after being cultured in a culture medium for iPS cells containing β-NMN was larger than that of the cells that have undergone ectodermal differentiation-induction after being cultured in a culture medium for iPS cells not containing β-NMN. That is, it was found that the addition of β-NMN during the undifferentiated culture improves cell proliferation during the subsequent ectodermal differentiation.
<Measurement of Cells Expressing Ectodermal Differentiation Marker Using Flow Cytometer>
In the same manner as in Example 2, the cells sampled on the 7th or 9th day after seeding were stained with a fluorescently labeled anti-Nestin antibody and a fluorescently labeled anti-PAX6 antibody, and a flow cytometer was used to analyze the fluorescence intensity of the anti-Nestin antibody and the fluorescence intensity of the anti-PAX6 antibody in each sample.

The results of fractionating each sample by the expression level of Nestin and PAX6 using a flow cytometer are shown in FIG. 11. The Nestin-positive and PAX6-positive cells are the cells differentiated into ectoderm. The percentages in the figure indicate the ratio (%) of Nestin-positive PAX6-positive cells to the total amount of cells. As a result, there was no clear difference in the ratio of Nestin-positive PAX6- positive cells after differentiation-induction between the cells cultured in the presence of β-NMN before ectodermal differentiation-induction and the cells cultured in the absence of β-NMN. That is, it was confirmed that β-NMN at the time of undifferentiated culture did not significantly affect the differentiation efficiency in the subsequent induction of ectodermal differentiation.

As shown in the results, by carrying out the ectodermal differentiation-induction of iPS cells after culturing the iPS cells in the presence of β-NMN in advance, the cell proliferative property at the time of ectodermal differentiation-induction was improved, but there was no clear difference in the differentiation from iPS cells into ectodermal cells.

Example 8

The effects of culturing in the presence of β-NMN before bone differentiation-induction of mesenchymal stern cells were examined. Human adipose tissue-derived mesenchymal stem cells (manufactured by Lonza, Cat #PT5006) were used as the mesenchymal stem cells.
<Culture Medium>
As a growth medium, a culture medium prepared by appropriately adding β-MNM to "MSCGM Bullet Kit" (manufactured by Lonza, Cat #PT3001) was used.

As a bone differentiation-inducing culture medium, a culture medium prepared by adjusting an α-MEM culture medium to have a final concentration of fetal bovine serum of 10% by volume, a final concentration of dexamethasone of 10 nM, a final concentration of β-glycerophosphate of 10 mM, a final concentration of ascorbic acid of 50 μg/mL, and a final concentration of penicillin-streptomycin of 0.1%.
<Culture of Mesenchymal Stem Cells>
The mesenchymal stem cells were seeded in a culture dish at $5 \times 10^3$ cells/cm$^2$ and statically cultured in a growth culture medium not containing β-MNM at 37° C., 5% by volume ($CO_2$) for 1 day. From one day after seeding, the culture medium was replaced every 2 days with a growth culture medium adjusted to have a final concentration of β-MNM of 0, 0.1, or 0.25 mM.

Further, when the cell density in the culture dish reached 80 to 90% of the confluent, the cells were passaged. For the passage, first, the supernatant was removed from the culture dish, washed with PBS, then "1× Tryple Select" (manufactured by Gibco) was added, and the mixture was allowed to stand at 37° C., 5% by volume ($CO_2$) for 4 minutes. After allowing to stand, the dish was tapped to exfoliate the cells, a growth culture medium was added, and the cells were singled by pipetting. Next, the singled cells were dispersed in a growth culture medium supplemented with β-MNM, seeded at $5 \times 10^3$ cells/cm$^2$ in a culture dish, and allowed to be statically cultured at 37° C. and 5% by volume ($CO^2$).

The cells passaged four times were used for the subsequent differentiation assay.
<Differentiation-Induction>
Cells acclimated to β-MNM were seeded in a 48-well plate at $2 \times 10^4$ cells/well, and cultured in a growth culture medium containing β-MNM at 37° C., 5% by volume ($CO^2$) until the cell density in the well reached 80 to 90% of confluent, and then the growth culture medium was replaced with a bone differentiation-induction medium. The exchange of culture medium was carried out once every 3 to 4 days, and a staining test was performed 14 days after the initiation of differentiation-induction.

<Staining Test>
Regarding the cells after differentiation-induction, the deposited calcium was stained with Alizarin Red S, and the stained state was confirmed with a phase contrast microscope.

Figure 14:
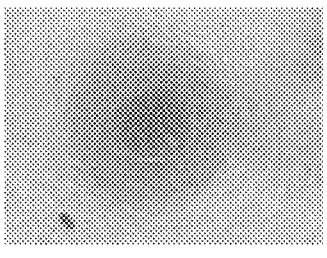
FIG. 14 is an Alizarin S-stained image of the differentiated cells obtained by bone differentiation-induction of mesenchymal stem cells cultured in a growth medium supplemented with the β-NMN in Example 8.
Figure 14:
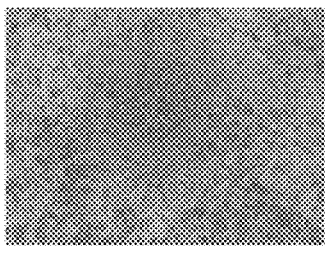
Figure 14:
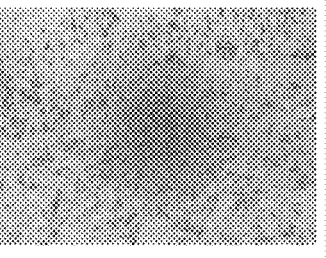

The stained image is shown in FIG. 14. The calcium deposition was strongly observed in the cells cultured in the medium supplemented with 0.1 mM or 0.25 mM of β-NMN as compared with the cells cultured in the medium without β-NMN (0 mM). From these results, it was found that the cells grown and cultured in the presence of β-NMN promoted the bone differentiation.

Example 9

The effects of culturing in the presence of β-NMN before adipocyte differentiation-induction of mesenchymal stern cells were examined. In the same manner as in Example 8, Human adipose tissue-derived mesenchymal stem cells (manufactured by Lonza, Cat #PT5006) were used as the mesenchymal stem cells.
<Culture Medium>
As a growth culture medium, a culture medium prepared by appropriately adding β-MNM to "MSCGM Bullet Kit" (manufactured by Lonza, Cat #PT3001) was used as in Example 8.

As an adipocyte differentiation-inducing culture medium, a culture medium prepared by adjusting a DMEM-High Glucose medium to have a final concentration of fetal bovine serum of 10% by volume, a final concentration of IBMX of 0.5 mM, a final concentration of dexamethasone of 1 μM, a final concentration of indomethacin of 200 μM, and a final concentration of penicillin-streptomycin of 0.1% was used.
<Culture of Mesenchymal Stem Cells>
The culture of the mesenchymal stem cells before differentiation-induction was performed in the same manner as in Example 8.
<Differentiation-Induction>
The differentiation induction was performed in the same manner as in Example 8 except that the adipocyte differentiation-inducing culture medium was used instead of the bone differentiation-inducing culture medium. On the 14th day from the initiation of the differentiation-induction, the staining test and the cell RNA recovery were performed.
<Staining Test>
Regarding the cells after differentiation-induction, the intracellular lipid droplets were stained with oil red O, and the stained state was confirmed with a phase contrast microscope.

Figure 15:
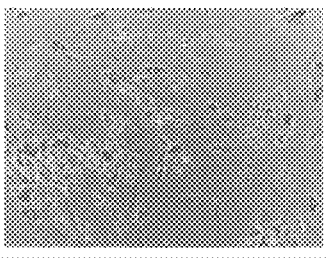
FIG. 15 is an oil red O-stained image of a differentiated cell obtained by adipose differentiation-induction of mesenchymal stem cells cultured in growth culture medium supplemented with the β-NMN in Example 9.
Figure 15:
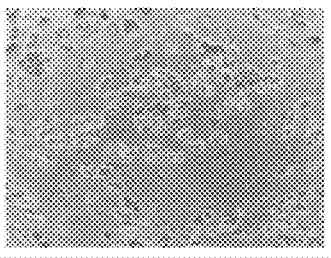
Figure 15:
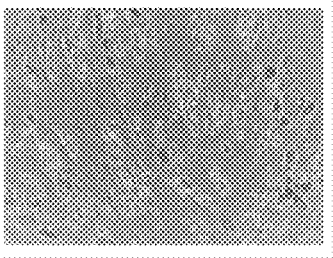

The stained image is shown in FIG. 15. The cells cultured in the medium supplemented with 0.1 mM or 0.25 mM of β-NMN showed more accumulation of lipid droplets as compared with the cells cultured in the medium without β-NMN (0 mM).
<qPCR Measurement>
From the cells after differentiation-induction, RNA was extracted using "RNeasy Mini Plus Kit" (manufactured by QIAGENE), and the extracted RNA was used as a template to synthesize cDNA using "SuperScript (registered trademark) III First-Strand Synthesis Super Mix" (manufactured by Invitrogen Corporation). The resulting cDNA was used as a template, and QPCR was performed using the primers shown in Table 1 and reagents "TB Green Fast qPCR Mix" (manufactured by TaKaRa Bio), thereby measuring the expression levels of PPARγ gene, Adipontin gene, and GAPDH gene. As the measuring instrument, a real-time PCR system "7500 Fast Real-Time PCR System" (manufactured by Applied Biosystems) was used. The GAPDH gene was used as an internal standard.

TABLE 1

| Primer | Sequence (5'→3') | Sequence No. |
|---|---|---|
| PPARγ | GAGCCCAAGTTTGAGTTTGC | 1 |
|  | TCAATGGGCTTCACATTCAG | 2 |
| Adiponectin | CCTGGTGAGAAGGGTGAGAA | 3 |
|  | CTCCTTTCCTGCCTTGGATT | 4 |
| GAPDH | AACGGGAAGCTTGTCATCAATGGAAA | 5 |
|  | GCATCAGCAGAGGGGCAGAG | 6 |

Figure 16:
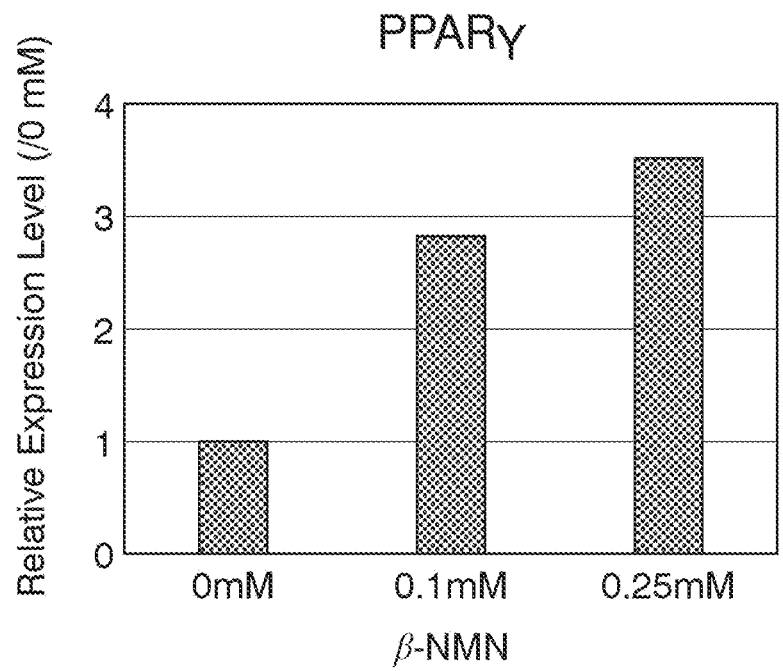
FIG. 16 is a diagram showing the results of measurement of the relative expression of the PPARγ gene in the differentiated cells obtained by adipose differentiation-induction of the mesenchymal stern cells cultured in a growth culture medium supplemented with the β-NMN in Example 9.
Figure 17:
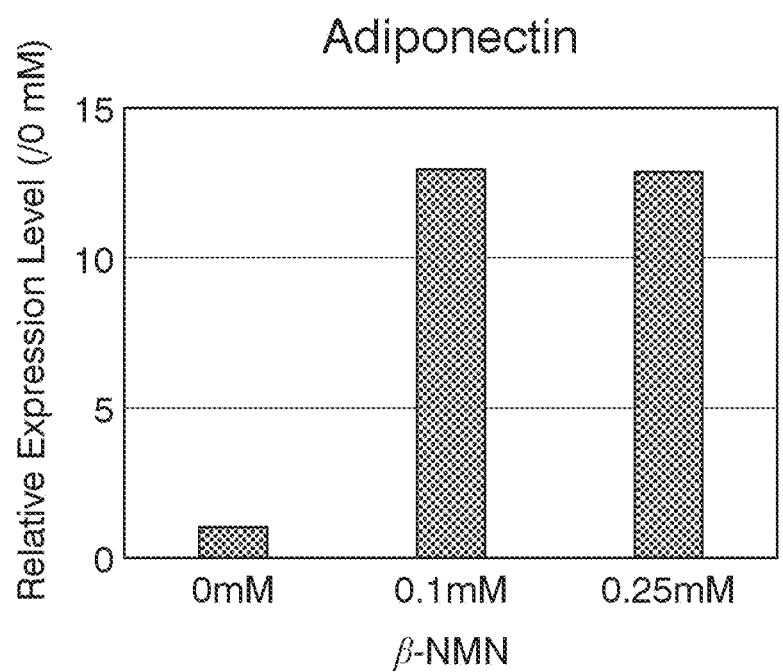
FIG. 17 is a diagram showing the results of the measurement of the relative expression of the adiponectin gene in the differentiated cells obtained by adipose differentiation-induction of the mesenchymal stem cells cultured in a growth culture medium supplemented with the β-NMN in Example 9.

The relative expression level of each gene was determined from the results of qPCR of cells that were induced to differentiate into adipocytes. The gene expression level of the cells cultured in the culture medium not containing β-NMN (0 mM) was defined as 1. FIG. 16 shows the measurement results of the relative expression level of the PPARγ gene, and FIG. 17 shows the measurement results of the relative expression level of the adiponectin gene. Both PPARγ and adiponectin are adipocyte differentiation markers. An increase in the expression level of both genes was confirmed in the cells cultured in the medium supplemented with 0.1 mM or 0.25 mM of β-NMN, as compared with the cells cultured in the culture medium not containing β-NMN (0 mM).

From the results of Oil Red O staining and qPCR, it was found that the cells grown and cultured in the presence of β-NMN promoted the adipocyte differentiation.

The invention claimed is:

1. A method for differentiating pluripotent stem cells, comprising culturing pluripotent stem cells in a culture medium containing a β-nicotinamide mononucleotide or a pharmacologically acceptable salt thereof, or a solvate thereof, wherein
the culture medium is a differentiation-inducing culture medium containing one or more differentiation-inducing factors that differentiate the pluripotent stem cells, and
the pluripotent stem cells are one or more cells selected from the group consisting of embryonic stem cells, artificial pluripotent stem cells, mesenchymal stem cells, hematopoietic stem cells, and skin stem cells.

2. The method according to claim 1, wherein the β-nicotinamide mononucleotide concentration of the culture medium is in a range from 0.01 to 10 mM.

3. The method according to claim 1, wherein the differentiation-inducing culture medium is a culture medium for differentiating the pluripotent stem cells into either endoderm, mesoderm, or ectoderm.

4. The method according to claim 1, wherein the pluripotent stem cells are cultured in a culture medium maintaining pluripotency and containing the β-nicotinamide mononucleotide or the pharmacologically acceptable salt thereof, or the solvate thereof, prior to the culturing pluripotent stem cells in the differentiation-inducing culture medium.

5. A method for promoting differentiation of pluripotent stem cells, comprising culturing pluripotent stem cells in a culture medium containing a β-nicotinamide mononucleotide or a pharmacologically acceptable salt thereof, or a solvate thereof, wherein
the culture medium is a differentiation-inducing culture medium containing one or more differentiation-inducing factors that differentiate the pluripotent stem cells, and
the pluripotent stem cells are one or more cells selected from the group consisting of embryonic stem cells, artificial pluripotent stem cells, mesenchymal stem cells, hematopoietic stem cells, and skin stem cells.

6. The method according to claim 2, wherein the β-nicotinamide mononucleotide concentration of the culture medium is in a range from 0.05 to 5 mM.

7. The method according to claim 6, wherein the β-nicotinamide mononucleotide concentration of the culture medium is in a range from 0.1 to 1 mM.

8. The method according to claim 1, wherein
the pluripotent stem cells are one or more cells selected from the group consisting of the embryonic stem cells, the artificial pluripotent stem cells, and the mesenchymal stem cells.

9. The method according to claim 8, wherein the differentiation-inducing culture medium is
a culture medium for differentiating the embryonic stem cells or the artificial pluripotent stem cells into endoderm, or
a culture medium for differentiating the mesenchymal stem cells into either bone or adipocyte.

10. The method according to claim 5, wherein the β-nicotinamide mononucleotide concentration of the culture medium is in a range from 0.01 to 10 mM.

11. The method according to claim 5, wherein the differentiation-inducing culture medium is a culture medium for differentiating the pluripotent stem cells into either endoderm, mesoderm, or ectoderm.

12. The method according to claim 5, wherein the pluripotent stem cells are cultured in a culture medium maintaining pluripotency and containing the β-nicotinamide mononucleotide or the pharmacologically acceptable salt thereof, or the solvate thereof, prior to the culturing the pluripotent stem cells in the differentiation-inducing culture medium.

13. The method according to claim 5, wherein the β-nicotinamide mononucleotide concentration of the culture medium is in a range from 0.05 to 5 mM.

14. The method according to claim 13, wherein the β-nicotinamide mononucleotide concentration of the culture medium is in a range from 0.1 to 1 mM.

15. The method according to claim 5, wherein
the pluripotent stem cells are one or more cells selected from the group consisting of the embryonic stem cells, the artificial pluripotent stem cells, and the mesenchymal stem cells.

16. The method according to claim 15, wherein the differentiation-inducing culture medium is
a culture medium for differentiating the embryonic stem cells or the artificial pluripotent stem cells into endoderm, or
a culture medium for differentiating the mesenchymal stem cells into either bone or adipocyte.

* * * * *